(12) United States Patent
Bucciaglia et al.

(10) Patent No.: US 9,364,247 B2
(45) Date of Patent: Jun. 14, 2016

(54) ENDOSCOPIC ELECTROSURGICAL JAWS WITH OFFSET KNIFE

(71) Applicant: COVIDIEN LP, Mansfield, MA (US)

(72) Inventors: Joesph D. Bucciaglia, Louisville, CO (US); Edward M. Chojin, Boulder, CO (US); Glenn A. Horner, Boulder, CO (US)

(73) Assignee: COVIDIEN LP, Mansfield, MA (US)

( * ) Notice: Subject to any disclaimer, the term of this patent is extended or adjusted under 35 U.S.C. 154(b) by 263 days.

(21) Appl. No.: 13/969,204

(22) Filed: Aug. 16, 2013

(65) Prior Publication Data

US 2013/0338666 A1    Dec. 19, 2013

Related U.S. Application Data

(63) Continuation of application No. 13/571,821, filed on Aug. 10, 2012, now Pat. No. 8,523,898, which is a continuation of application No. 12/499,553, filed on Jul. 8, 2009, now Pat. No. 8,246,618.

(51) Int. Cl.
*A61B 18/14*     (2006.01)
*A61B 17/32*     (2006.01)
(Continued)

(52) U.S. Cl.
CPC .............. *A61B 17/32* (2013.01); *A61B 17/295* (2013.01); *A61B 17/2909* (2013.01); *A61B 18/1445* (2013.01); *A61N 1/18* (2013.01); *A61B 2017/2911* (2013.01); *A61B 2017/2919* (2013.01); *A61B 2017/2922* (2013.01);
(Continued)

(58) Field of Classification Search
CPC ............. A61B 2018/00214; A61B 2018/0022; A61B 2018/00488; A61B 18/1445; A61B 2017/2932; A61B 2017/2926; A61B 2017/2939; A61B 2017/2933
USPC ................................................ 606/20–26, 51
See application file for complete search history.

(56) References Cited

U.S. PATENT DOCUMENTS

| 371,664 A | 10/1887 | Brannan et al. |
| 702,472 A | 6/1902 | Pignolet |

(Continued)

FOREIGN PATENT DOCUMENTS

| JP | 61-501068 | 9/1984 |
| JP | 11-192238 A | 7/1999 |

(Continued)

OTHER PUBLICATIONS

U.S. Appl. No. 08/926,869, filed Sep. 10, 1997, James G. Chandler.

(Continued)

*Primary Examiner* — Michael Peffley

(57) ABSTRACT

A forceps includes an end effector assembly having first and second jaw members. Each jaw member includes a proximal flange having an inwardly-facing surface. The proximal flanges are coupled to one another for moving the jaw members relative to one another between a first position and a second position for grasping tissue therebetween. The inwardly-facing surfaces of the proximal flanges are disposed in abutting relation relative to one another. A knife is configured to move along a knife path defined along an outwardly-facing surface of one of the proximal flanges. The knife is movable between a retracted position and an extended position, wherein the knife extends between the jaw members to cut tissue grasped therebetween.

20 Claims, 11 Drawing Sheets

(51) Int. Cl.
  *A61B 17/29* (2006.01)
  *A61B 17/295* (2006.01)
  *A61N 1/18* (2006.01)
  *A61B 18/00* (2006.01)

(52) U.S. Cl.
  CPC .............. *A61B2017/2945* (2013.01); *A61B 2017/320052* (2013.01); *A61B 2018/0063* (2013.01); *A61B 2018/00404* (2013.01); *A61B 2018/00601* (2013.01); *A61B 2018/1412* (2013.01); *A61B 2018/1432* (2013.01); *A61B 2018/1455* (2013.01)

(56) References Cited

U.S. PATENT DOCUMENTS

| | | |
|---|---|---|
| 728,883 A | 5/1903 | Downes |
| 1,586,645 A | 6/1926 | Bierman |
| 1,813,902 A | 7/1931 | Bovie |
| 1,822,330 A | 9/1931 | Ainslie |
| 1,852,542 A | 4/1932 | Sovatkin |
| 1,908,201 A | 5/1933 | Welch et al. |
| 1,918,889 A | 7/1933 | Bacon |
| 2,002,594 A | 5/1935 | Wappler et al. |
| 2,011,169 A | 8/1935 | Wappler |
| 2,031,682 A | 2/1936 | Wappler et al. |
| 2,054,149 A | 9/1936 | Wappler |
| 2,113,246 A | 5/1937 | Wappler |
| 2,141,936 A | 12/1938 | Schmitt |
| 2,176,479 A | 10/1939 | Willis |
| 2,245,030 A | 6/1941 | Gottesfeld et al. |
| 2,279,753 A | 4/1942 | Knopp |
| 2,305,156 A | 12/1942 | Grubel |
| 2,327,353 A | 8/1943 | Karle |
| 2,632,661 A | 3/1953 | Cristofv |
| 2,668,538 A | 2/1954 | Baker |
| 2,796,065 A | 6/1957 | Kapp |
| 2,824,915 A | 2/1958 | Buturuga |
| 3,073,311 A | 1/1963 | Tibbs et al. |
| 3,100,489 A | 8/1963 | Bagley |
| 3,204,807 A | 9/1965 | Ramsing |
| 3,372,288 A | 3/1968 | Wigington |
| 3,459,187 A | 8/1969 | Pallotta |
| 3,561,448 A | 2/1971 | Peternel |
| 3,643,663 A | 2/1972 | Sutter |
| 3,648,001 A | 3/1972 | Anderson et al. |
| 3,651,811 A | 3/1972 | Hildebrandt et al. |
| 3,678,229 A | 7/1972 | Osika |
| 3,720,896 A | 3/1973 | Beierlein |
| 3,763,726 A | 10/1973 | Hildebrand |
| 3,779,918 A | 12/1973 | Ikeda et al. |
| 3,798,688 A | 3/1974 | Wasson |
| 3,801,766 A | 4/1974 | Morrison, Jr. |
| 3,839,614 A | 10/1974 | Saganowski et al. |
| D249,549 S | 9/1978 | Pike |
| D263,020 S | 2/1982 | Rau, III |
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| D343,453 S | 1/1994 | Noda |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| 5,568,859 A | 10/1996 | Levy et al. |
| 5,569,241 A | 10/1996 | Edwards |
| 5,569,243 A | 10/1996 | Kortenbach et al. |
| 5,571,100 A | 11/1996 | Goble et al. |
| 5,573,424 A | 11/1996 | Poppe |
| 5,573,534 A | 11/1996 | Stone |
| 5,573,535 A | 11/1996 | Viklund |
| 5,575,799 A | 11/1996 | Bolanos et al. |
| 5,575,805 A | 11/1996 | Li |
| 5,578,052 A | 11/1996 | Koros et al. |
| 5,579,781 A | 12/1996 | Cooke |
| 5,582,611 A | 12/1996 | Tsuruta et al. |
| 5,582,617 A | 12/1996 | Klieman et al. |
| 5,585,896 A | 12/1996 | Yamazaki et al. |
| 5,590,570 A | 1/1997 | LeMaire, III et al. |
| 5,591,181 A | 1/1997 | Stone et al. |
| 5,597,107 A | 1/1997 | Knodel et al. |
| 5,599,350 A | 2/1997 | Schulze et al. |
| 5,601,224 A | 2/1997 | Bishop et al. |
| 5,601,601 A | 2/1997 | Tal et al. |
| 5,601,641 A | 2/1997 | Stephens |
| 5,603,711 A | 2/1997 | Parins et al. |
| 5,603,723 A | 2/1997 | Aranyi et al. |
| 5,607,436 A | 3/1997 | Pratt et al. |
| 5,611,798 A | 3/1997 | Eggers |
| 5,611,808 A | 3/1997 | Hossain et al. |
| 5,611,813 A | 3/1997 | Lichtman |
| 5,618,294 A | 4/1997 | Aust et al. |
| 5,618,307 A | 4/1997 | Donlon et al. |
| 5,620,415 A | 4/1997 | Lucey et al. |
| 5,620,453 A | 4/1997 | Nallakrishnan |
| 5,620,459 A | 4/1997 | Lichtman |
| 5,624,281 A | 4/1997 | Christensson |
| 5,624,452 A | 4/1997 | Yates |
| 5,626,578 A | 5/1997 | Tihon |
| 5,626,607 A | 5/1997 | Malecki et al. |
| 5,626,609 A | 5/1997 | Zvenyatsky et al. |
| 5,630,833 A | 5/1997 | Katsaros et al. |
| 5,637,110 A | 6/1997 | Pennybacker et al. |
| 5,637,111 A * | 6/1997 | Sutcu et al. ............ 606/51 |
| 5,638,827 A | 6/1997 | Palmer et al. |
| D384,413 S | 9/1997 | Zlock et al. |
| D402,028 S | 12/1998 | Grimm et al. |
| D408,018 S | 4/1999 | McNaughton |
| 5,908,420 A * | 6/1999 | Parins et al. ............ 606/51 |
| D416,089 S | 11/1999 | Barton et al. |
| D424,694 S | 5/2000 | Tetzlaff et al. |
| D425,201 S | 5/2000 | Tetzlaff et al. |
| RE36,795 E | 7/2000 | Rydell |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| 6,385,265 B1 | 5/2002 | Duffy et al. |
| 6,387,094 B1 | 5/2002 | Eitenmuller |
| 6,391,035 B1 | 5/2002 | Appleby et al. |
| 6,398,779 B1 | 6/2002 | Buysse et al. |
| 6,402,747 B1 | 6/2002 | Lindemann et al. |
| 6,409,728 B1 | 6/2002 | Ehr et al. |
| 6,419,675 B1 | 7/2002 | Gallo, Sr. |
| 6,425,896 B1 | 7/2002 | Baltschun et al. |
| 6,432,112 B2 | 8/2002 | Brock et al. |
| 6,440,130 B1 | 8/2002 | Mulier et al. |
| 6,440,144 B1 | 8/2002 | Bacher |
| 6,443,952 B1 | 9/2002 | Mulier et al. |
| 6,443,970 B1 | 9/2002 | Schulze et al. |
| 6,451,018 B1 | 9/2002 | Lands et al. |
| 6,458,125 B1 | 10/2002 | Cosmescu |
| 6,458,128 B1 | 10/2002 | Schulze |
| 6,458,129 B2 | 10/2002 | Scarfi |
| 6,458,130 B1 | 10/2002 | Frazier et al. |
| 6,461,352 B2 | 10/2002 | Morgan et al. |
| 6,461,368 B2 | 10/2002 | Fogarty et al. |
| 6,464,701 B1 | 10/2002 | Hooven et al. |
| 6,464,702 B2 | 10/2002 | Schulze et al. |
| 6,464,704 B2 | 10/2002 | Schmaltz et al. |
| 6,471,696 B1 | 10/2002 | Berube et al. |
| D465,281 S | 11/2002 | Lang |
| D466,209 S | 11/2002 | Bon |
| 6,485,489 B2 | 11/2002 | Teirstein et al. |
| 6,488,680 B1 | 12/2002 | Francischelli et al. |
| 6,494,882 B1 | 12/2002 | Lebouitz et al. |
| 6,494,888 B1 | 12/2002 | Laufer et al. |
| 6,500,176 B1 | 12/2002 | Truckai et al. |
| 6,506,196 B1 | 1/2003 | Laufer |
| 6,508,815 B1 | 1/2003 | Strul et al. |
| 6,511,480 B1 | 1/2003 | Tetzlaff et al. |
| 6,514,215 B1 | 2/2003 | Ouchi |

(56) References Cited

U.S. PATENT DOCUMENTS

| | | | |
|---|---|---|---|
| 6,514,252 B2 | 2/2003 | Nezhat et al. | |
| 6,517,536 B2 | 2/2003 | Hooven et al. | |
| 6,517,539 B1 | 2/2003 | Smith et al. | |
| 6,527,771 B1 | 3/2003 | Weadock et al. | |
| 6,533,784 B2 | 3/2003 | Truckai et al. | |
| 6,537,272 B2 | 3/2003 | Christopherson et al. | |
| 6,540,745 B1 | 4/2003 | Fairbourn et al. | |
| 6,545,239 B2 | 4/2003 | Spedale et al. | |
| 6,767,349 B2* | 7/2004 | Ouchi | 606/51 |
| D493,888 S | 8/2004 | Reschke | |
| D496,997 S | 10/2004 | Dycus et al. | |
| D499,181 S | 11/2004 | Dycus et al. | |
| D502,994 S | 3/2005 | Blake, III | |
| D509,297 S | 9/2005 | Wells | |
| 6,951,560 B1* | 10/2005 | Kidooka | 606/51 |
| D525,361 S | 7/2006 | Hushka | |
| 7,083,618 B2* | 8/2006 | Couture et al. | 606/51 |
| D531,311 S | 10/2006 | Guerra et al. | |
| 7,131,970 B2* | 11/2006 | Moses | A61B 18/1442 606/205 |
| D533,274 S | 12/2006 | Visconti et al. | |
| D533,942 S | 12/2006 | Kerr et al. | |
| D535,027 S | 1/2007 | James et al. | |
| D538,932 S | 3/2007 | Malik | |
| D541,418 S | 4/2007 | Schechter et al. | |
| D541,611 S | 5/2007 | Aglassinger | |
| D541,938 S | 5/2007 | Kerr et al | |
| D545,432 S | 6/2007 | Watanabe | |
| D547,154 S | 7/2007 | Lee | |
| D564,662 S | 3/2008 | Moses et al. | |
| 7,422,592 B2* | 9/2008 | Morley | A61B 18/1445 606/49 |
| 7,628,791 B2 | 12/2009 | Garrison et al. | |
| 7,628,792 B2 | 12/2009 | Guerra | |
| 7,637,409 B2 | 12/2009 | Marczyk | |
| 7,641,653 B2 | 1/2010 | Dalla Betta et al. | |
| 7,651,493 B2 | 1/2010 | Arts et al. | |
| 7,651,494 B2 | 1/2010 | McClurken et al. | |
| 7,655,004 B2 | 2/2010 | Long | |
| 7,655,007 B2 | 2/2010 | Baily | |
| 7,668,597 B2 | 2/2010 | Engmark et al. | |
| 7,678,111 B2 | 3/2010 | Mulier et al. | |
| 7,686,804 B2 | 3/2010 | Johnson et al. | |
| 7,686,827 B2 | 3/2010 | Hushka | |
| 7,708,735 B2 | 5/2010 | Chapman et al. | |
| 7,717,115 B2 | 5/2010 | Barrett et al. | |
| 7,717,904 B2 | 5/2010 | Suzuki et al. | |
| 7,717,914 B2 | 5/2010 | Kimura | |
| 7,717,915 B2 | 5/2010 | Miyazawa | |
| 7,722,607 B2 | 5/2010 | Dumbauld et al. | |
| 7,727,231 B2 | 6/2010 | Swanson | |
| 7,731,717 B2 | 6/2010 | Odom et al. | |
| 7,736,374 B2 | 6/2010 | Vaughan et al. | |
| 7,744,615 B2 | 6/2010 | Couture | |
| 7,749,217 B2 | 7/2010 | Podhajsky | |
| 7,753,908 B2 | 7/2010 | Swanson | |
| 7,753,909 B2 | 7/2010 | Chapman et al. | |
| 7,766,910 B2 | 8/2010 | Hixson et al. | |
| 7,771,425 B2 | 8/2010 | Dycus et al. | |
| 7,776,036 B2 | 8/2010 | Schechter et al. | |
| 7,776,037 B2 | 8/2010 | Odom | |
| 7,780,662 B2 | 8/2010 | Bahney | |
| 7,780,663 B2 | 8/2010 | Yates et al. | |
| 7,789,878 B2 | 9/2010 | Dumbauld et al. | |
| 7,799,026 B2 | 9/2010 | Schechter et al. | |
| 7,799,028 B2 | 9/2010 | Schechter et al. | |
| 7,806,892 B2 | 10/2010 | Makin et al. | |
| 7,811,283 B2 | 10/2010 | Moses et al. | |
| 7,819,872 B2 | 10/2010 | Johnson et al. | |
| 7,828,798 B2 | 11/2010 | Buysse et al. | |
| 7,832,408 B2 | 11/2010 | Shelton, IV et al. | |
| 7,837,685 B2 | 11/2010 | Weinberg et al. | |
| 7,839,674 B2 | 11/2010 | Lowrey et al. | |
| 2003/0109875 A1* | 6/2003 | Tetzlaff | A61B 18/1445 606/48 |
| 2007/0173814 A1* | 7/2007 | Hixson et al. | 606/51 |

FOREIGN PATENT DOCUMENTS

| | | | |
|---|---|---|---|
| JP | 11244298 A | 9/1999 | |
| JP | 2000-102545 A | 4/2000 | |
| JP | 2000342599 A | 12/2000 | |
| JP | 2000350732 A | 12/2000 | |
| JP | 2001008944 A | 1/2001 | |
| JP | 2001029356 A | 2/2001 | |
| JP | 2001-03400 | 4/2001 | |
| JP | 2001128990 A | 5/2001 | |
| JP | 2001-190564 A | 7/2001 | |
| JP | 2002-136525 A | 5/2002 | |
| JP | 2002-528166 A | 9/2002 | |
| JP | 2003-175052 A | 6/2003 | |
| JP | 2003245285 A | 9/2003 | |
| JP | 2004-517668 A | 6/2004 | |
| JP | 2004-528869 A | 9/2004 | |
| JP | 2005-253789 A | 9/2005 | |
| JP | 2006-015078 A | 1/2006 | |
| JP | 2006-501939 A | 1/2006 | |
| JP | 2006-095316 A | 4/2006 | |
| JP | 2011125195 A | 6/2011 | |
| SU | 401367 A1 | 10/1973 | |
| WO | 0036986 A1 | 6/2000 | |
| WO | 0059392 A1 | 10/2000 | |
| WO | 0115614 A1 | 3/2001 | |
| WO | 0154604 A1 | 8/2001 | |
| WO | 02045589 A3 | 9/2002 | |
| WO | 2006/021269 A1 | 3/2006 | |
| WO | 2005110264 A3 | 4/2006 | |
| WO | 2008/040483 A1 | 4/2008 | |

OTHER PUBLICATIONS

U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 9, 2000, Thomas P. Ryan.
U.S. Appl. No. 12/336,970, filed Dec. 17, 2008, Paul R. Sremcich.
U.S. Appl. No. 13/050,182, filed Mar. 17, 2011, Glenn A. Horner.
U.S. Appl. No. 13/072,945, filed Mar. 28, 2011, Patrick L. Dumbauld.
U.S. Appl. No. 13/080,383, filed Apr. 5, 2011, David M. Garrison.
U.S. Appl. No. 13/085,144, filed Apr. 12, 2011, Keir Hart.
U.S. Appl. No. 13/091,331, filed Apr. 21, 2011, Jeffrey R. Townsend.
U.S. Appl. No. 13/102,573, filed May 6, 2011, John R. Twomey.
U.S. Appl. No. 13/102,604, filed May 6, 2011, Paul E. Ourada.
U.S. Appl. No. 13/108,093, filed May 16, 2011, Boris Chernov.
U.S. Appl. No. 13/108,129, filed May 16, 2011, Boris Chernov.
U.S. Appl. No. 13/108,152, filed May 16, 2011, Boris Chernov.
U.S. Appl. No. 13/108,177, filed May 16, 2011, Boris Chernov.
U.S. Appl. No. 13/108,196, filed May 16, 2011, Boris Chernov.
U.S. Appl. No. 13/108,441, filed May 16, 2011, Boris Chernov.
U.S. Appl. No. 13/108,468, filed May 16, 2011, Boris Chernov.
U.S. Appl. No. 13/111,642, filed May 16, 2011, John R. Twomey.
U.S. Appl. No. 13/111,678, filed May 19, 2011, Nikolay Kharin.
U.S. Appl. No. 13/113,231, filed May 23, 2011, David M. Garrison.
U.S. Appl. No. 13/157,047, filed Jun. 9, 2011, John R. Twomey.
U.S. Appl. No. 13/162,814, filed Jun. 17, 2011, Barbara R. Tyrrell.
U.S. Appl. No. 13/166,477, filed Jun. 22, 2011, Daniel A. Joseph.
U.S. Appl. No. 13/166,497, filed Jun. 22, 2011, Daniel A. Joseph.
U.S. Appl. No. 13/179,919, filed Jun. 11, 2011, Russell D. Hempstead.
U.S. Appl. No. 13/179,960, filed Jul. 11, 2011, Boris Chernov.
U.S. Appl. No. 13/179,975, filed Jul. 11, 2011, Grant T. Sims.
U.S. Appl. No. 13/180,018, filed Jul. 11, 2011, Chase Collings.
U.S. Appl. No. 13/183,856, filed Jul. 15, 2011, John R. Twomey.
U.S. Appl. No. 13/185,593, filed Jul. 19, 2011, James D. Allen, IV.
U.S. Appl. No. 13/204,841, filed Aug. 8, 2011, Edward J. Chojin.
U.S. Appl. No. 13/205,999, filed Aug. 9, 2011, Jeffrey R. Unger.
U.S. Appl. No. 13/212,297, filed Aug. 18, 2011, Allan J. Evans.
U.S. Appl. No. 13/212,308, filed Aug. 18, 2011, Allan J. Evans.

(56) References Cited

OTHER PUBLICATIONS

U.S. Appl. No. 13/212,329, filed Aug. 18, 2011, Allan J. Evans.
U.S. Appl. No. 13/212,343, filed Aug. 18, 2011, Duane E. Kerr.
U.S. Appl. No. 13/223,521, filed Sep. 1, 2011, John R. Twomey.
U.S. Appl. No. 13/227,220, filed Sep. 7, 2011, James D. Allen, IV.
U.S. Appl. No. 13/228,742, filed Sep. 9, 2011, Duane E. Kerr.
U.S. Appl. No. 13/231,643, filed Sep. 13, 2011, Keir Hart.
U.S. Appl. No. 13/234,357, filed Sep. 16, 2011, James D. Allen, IV.
U.S. Appl. No. 13/236,168, filed Sep. 19, 2011, James D. Allen, IV.
U.S. Appl. No. 13/236,271, filed Sep. 19, 2011, Monte S. Fry.
U.S. Appl. No. 13/243,628, filed Sep. 23, 2011, William Ross Whitney.
U.S. Appl. No. 13/247,778, filed Sep. 28, 2011, John R. Twomey.
U.S. Appl. No. 13/247,795, filed Sep. 28, 2011, John R. Twomey.
U.S. Appl. No. 13/248,976, filed Sep. 29, 2011, James D. Allen, IV.
U.S. Appl. No. 13/249,013, filed Sep. 29, 2011, Jeffrey R. Unger.
U.S. Appl. No. 13/249,024, filed Sep. 29, 2011, John R. Twomey.
U.S. Appl. No. 13/251,380, filed Oct. 3, 2011, Duane E. Kerr.
U.S. Appl. No. 13/277,373, filed Oct. 20, 2011, Glenn A. Horner.
U.S. Appl. No. 13/277,926, filed Oct. 20, 2011, David M. Garrison.
U.S. Appl. No. 13/277,962, filed Oct. 20, 2011, David M. Garrison.
U.S. Appl. No. 13/293,754, filed Nov. 10, 2011, Jeffrey M. Roy.
U.S. Appl. No. 13/306,523, filed Nov. 29, 2011, David M. Garrison.
U.S. Appl. No. 13/306,553, filed Nov. 29, 2011, Duane E. Kerr.
U.S. Appl. No. 13/308,104, filed Nov. 30, 2011, John R. Twomey.
U.S. Appl. No. 13/312,172, filed Dec. 6, 2011, Robert J. Behnke, II.
U.S. Appl. No. 13/324,863, filed Dec. 13, 2011, William H. Nau, Jr.
U.S. Appl. No. 13/344,729, filed Jan. 6, 2012, James D. Allen, IV.
U.S. Appl. No. 13/355,829, filed Jan. 23, 2012, John R. Twomey.
U.S. Appl. No. 13/357,979, filed Jan. 25, 2012, David M. Garrison.
U.S. Appl. No. 13/358,136, filed Jan. 25, 2012, James D. Allen, IV.
U.S. Appl. No. 13/360,925, filed Jan. 30, 2012, James H. Orszulak.
U.S. Appl. No. 13/400,290, filed Feb. 20, 2012, Eric R. Larson.
U.S. Appl. No. 13/404,435, filed Feb. 24, 2012, Kim V. Brandt.
U.S. Appl. No. 13/404,476, filed Feb. 24, 2012, Kim V. Brandt.
U.S. Appl. No. 13/412,879, filed Mar. 6, 2012, David M. Garrison.
U.S. Appl. No. 13/412,897, filed Mar. 6, 2012, Joanna Ackley.
U.S. Appl. No. 13/421,373, filed Mar. 15, 2012, John R. Twomey.
U.S. Appl. No. 13/430,325, filed Mar. 26, 2012, William H. Nau, Jr.
U.S. Appl. No. 13/433,924, filed Mar. 29, 2012, Keir Hart.
U.S. Appl. No. 13/448,577, filed Apr. 17, 2012, David M. Garrison.
U.S. Appl. No. 13/460,455, filed Apr. 30, 2012, Luke Waaler.
U.S. Appl. No. 13/461,335, filed May 1, 2012, James D. Allen, IV.
U.S. Appl. No. 13/461,378, filed May 1, 2012, James D. Allen, IV.
U.S. Appl. No. 13/461,397, filed May 1, 2012, James R. Unger.
U.S. Appl. No. 13/461,410, filed May 1, 2012, James R. Twomey.
U.S. Appl. No. 13/464,569, filed May 4, 2012, Duane E. Kerr.
U.S. Appl. No. 13/466,274, filed May 8, 2012, Stephen M. Kendrick.
U.S. Appl. No. 13/467,767, filed May 9, 2012, Duane E. Kerr.
U.S. Appl. No. 13/470,543, filed May 14, 2012, Sean T. Dycus.
U.S. Appl. No. 13/470,775, filed May 14, 2012, James D. Allen, IV.
U.S. Appl. No. 13/470,797, filed May 14, 2012, John J. Kappus.
U.S. Appl. No. 13/482,589, filed May 29, 2012, Eric R. Larson.
U.S. Appl. No. 13/483,733, filed May 30, 2012, Dennis W. Butcher.
U.S. Appl. No. 13/488,093, filed Jun. 4, 2012, Kristin D. Johnson.
U.S. Appl. No. 13/491,853, filed Jun. 8, 2012, Jessica E. Olson.
U.S. Appl. No. 13/537,517, filed Jun. 29, 2012, David N. Heard.
U.S. Appl. No. 13/537,577, filed Jun. 29, 2012, Tony Moua.
U.S. Appl. No. 13/550,322, filed Jul. 16, 2012, John J. Kappus.
U.S. Appl. No. 13/571,055, filed Aug. 9, 2012, Paul Guerra.
U.S. Appl. No. 13/571,821, filed Aug. 10, 2012, Joseph D. Bucciaglia.
U.S. Appl. No. 13/584,194, filed Aug. 13, 2012, Sean T. Dycus.

\* cited by examiner

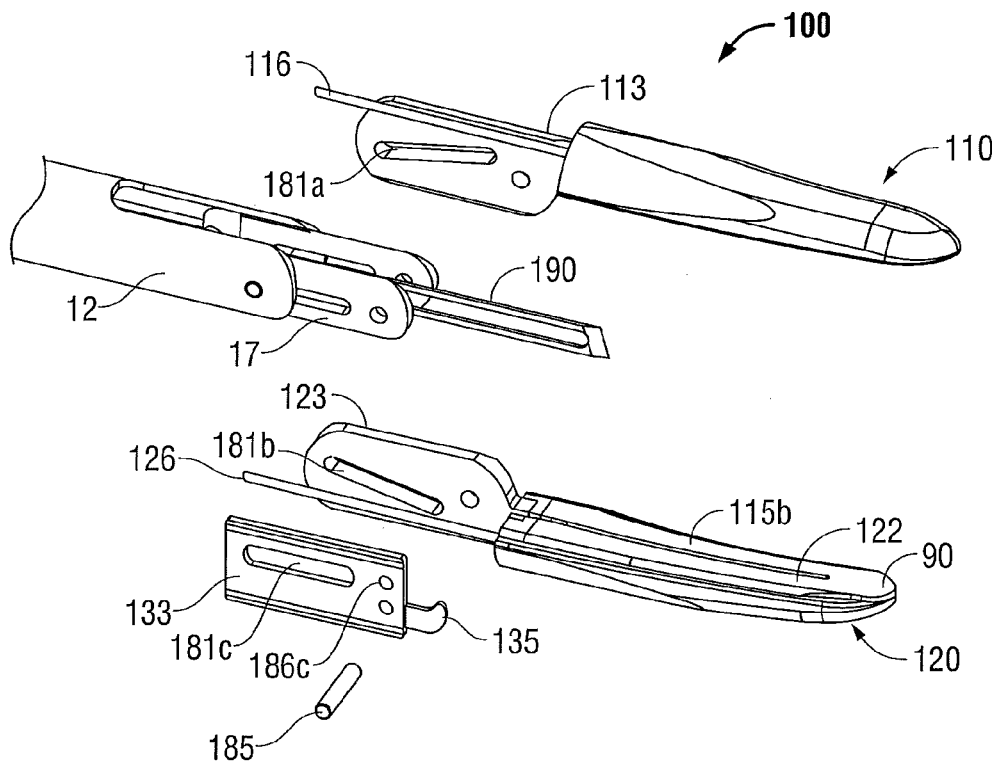
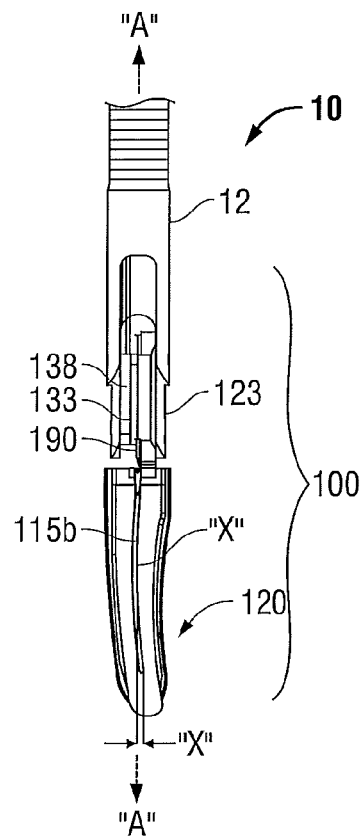
FIG. 6
FIG. 7

ENDOSCOPIC ELECTROSURGICAL JAWS WITH OFFSET KNIFE

CROSS-REFERENCE TO RELATED APPLICATIONS

This application is a continuation application of U.S. patent application Ser. No. 13/571,821, filed on Aug. 10, 2012, now U.S. Pat. No. 8,523,898, which is a continuation application of U.S. application Ser. No. 12/499,553, filed on Jul. 8, 2009. Now U.S. Pat. No. 8,246,618, the entire contents of each of which are hereby incorporated by reference herein.

BACKGROUND

1. Technical Field

The present disclosure relates to an electrosurgical jaws and, more particularly, to an elongated endoscopic electrosurgical forceps with an offset knife for sealing and/or cutting tissue.

2. Background of Related Art

Electrosurgical forceps utilize both mechanical clamping action and electrical energy to effect hemostasis by heating tissue and blood vessels to coagulate, cauterize and/or seal tissue. As an alternative to open forceps for use with open surgical procedures, many modern surgeons use endoscopic or laparoscopic instruments for remotely accessing organs through smaller, puncture-like incisions or natural orifices. As a direct result thereof, patients tend to benefit from less scarring and reduced healing time.

Endoscopic instruments are inserted into the patient through a cannula, or port, which has been made with a trocar. Typical sizes for cannulas range from three millimeters to twelve millimeters. Smaller cannulas are usually preferred, which, as can be appreciated, ultimately presents a design challenge to instrument manufacturers who must find ways to make endoscopic instruments that fit through the smaller cannulas.

Many endoscopic surgical procedures require cutting or ligating blood vessels or vascular tissue. Due to the inherent spatial considerations of the surgical cavity, surgeons often have difficulty suturing vessels or performing other traditional methods of controlling bleeding, e.g., clamping and/or tying-off transected blood vessels. By utilizing an endoscopic electrosurgical forceps, a surgeon can either cauterize, coagulate/desiccate and/or simply reduce or slow bleeding simply by controlling the intensity, frequency and duration of the electrosurgical energy applied through the jaw members to the tissue. Most small blood vessels, i.e., in the range below two millimeters in diameter, can often be closed using standard electrosurgical instruments and techniques. However, if a larger vessel is ligated, it may be necessary for the surgeon to convert the endoscopic procedure into an open-surgical procedure and thereby abandon the benefits of endoscopic surgery. Alternatively, the surgeon can seal the larger vessel or tissue.

Typically, after a vessel or tissue is sealed, the surgeon advances a knife to sever the sealed tissue disposed between the opposing jaw members. In some instances, the knife blade is difficult to advance through the knife channel defined between jaw members or is subject to wear and tear over repeated use due to the relative position of the knife blade through the knife channel (contacting the sides of the knife channel).

SUMMARY

The present disclosure relates to an endoscopic forceps that includes a housing having a shaft attached thereto with a longitudinal axis defined therethrough. An end effector assembly is disposed at a distal end thereof and includes first and second jaw members disposed in opposing relation relative to one another and moveable from a first, open position to a second, closed position for grasping tissue therebetween. Each of the jaw members includes a proximal flange adapted to communicate with a drive assembly for moving the jaw members between the first and second positions. One or both of the of the jaw members has a curved knife channel (or a portion, e.g., distal portion, of the knife channel is curved) defined therein having a proximal end that is offset from the longitudinal axis defined through the shaft. A knife guide is assembled to an outer surface of one of the proximal flanges of the jaw members on the same side as the proximal end of the knife channel and defines a knife path therein configured to guide a knife into the knife channel for translation therethrough. One or more handles may be included that operably couple to the drive assembly for moving the jaw members between the first and second positions.

In one embodiment, the endoscopic forceps is an electrosurgical instrument and at least one of the jaw members is adapted to connect to an electrosurgical energy source to communicate energy to tissue disposed between the jaw members.

In another embodiment, the proximal flanges of the end effector and the knife guide include elongated slots defined therethrough that cooperate with a drive pin operably connected to the drive assembly to move the jaw members from the first to second positions. The elongated slots of the proximal flanges may be cam slots that operably engage the drive pin and the elongated slot of the knife guide may be a pass-through or non-engaging slot.

In yet another embodiment, the offset knife channel and the disposition of the knife guide relative to the longitudinal axis facilitate substantially straight extension of the knife through the knife channel along a substantial length of the knife channel. This configuration helps prevent binding of the knife during translation through the knife channel. The proximal end of the knife channel may be offset a distance "X" relative to the longitudinal axis "A" defined through the forceps, wherein "X" is in the range of about 0.010 inches to about 0.040 inches. The knife channel may be defined within both the first and second jaw members and the knife guide is configured to preload the jaw members during assembly for ensuring proper alignment of the knife channels to facilitate translation of the knife therethrough.

In still yet another embodiment, the knife guide includes one or more channels defined therein that are configured to guide a corresponding number of electrical leads to the jaw member(s) for supplying electrosurgical energy thereto.

The present disclosure also relates to an endoscopic forceps that includes a housing having a shaft attached thereto with a longitudinal axis defined therethrough and an end effector assembly disposed at a distal end thereof. The end effector assembly includes first and second jaw members disposed in opposing relation relative to one another and moveable from a first, open configuration to a second, closed configuration for grasping tissue therebetween. Each of the jaw members includes a proximal flange adapted to communicate with a drive assembly for moving the jaw members between the first and second positions. One or both of the of the jaw members has a knife channel defined therein having a proximal end that is offset from the longitudinal axis defined through the shaft. A knife guide is assembled to an outer surface of one of the proximal flanges of the jaw members on the same side as the proximal end of the knife channel and defines a knife path therein configured to guide a knife into the knife channel for translation therethrough. The knife guide includes a blade stop at a distal end thereof that is positionable from a first position that interferes with or obstructs the knife path to prevent distal translation of the knife when the jaw members are disposed in an first, open configuration to a second position that allows distal translation of the knife when the jaw members are disposed in the second, closed configuration. The blade stop may be pivotably engaged to the knife guide and biased to obstruct the knife path when the jaw members are disposed in the first, open configuration.

The forceps may include one or more handles that operably couple to a drive assembly for moving the jaw members between the first and second configurations. Moreover, the forceps may be an electrosurgical forceps wherein one or both of the jaw members are adapted to connect to an electrosurgical energy source to communicate energy to tissue disposed between the jaw members.

The proximal flanges of the end effector and the knife guide may include elongated slots defined therethrough that cooperate with a drive pin operably connected to the drive assembly to move the jaw members from the first to second configurations. The elongated slots of the proximal flanges may be cam slots that operably engage the drive pin and the elongated slot of the knife guide may be a pass-through or non-engaging slot.

In another embodiment, the offset knife channel and the disposition of the knife guide relative to the longitudinal axis may be configured to facilitate substantially straight extension of the knife through the knife channel along a substantial length of the knife channel. The proximal end of the knife channel may be offset a distance "X" relative to the longitudinal axis "A" defined through the forceps, wherein "X" is in the range of about 0.010 inches to about 0.040 inches.

In yet another embodiment, the knife guide includes one or more channels defined therein that are configured to guide a corresponding number of electrical leads to the jaw member for supplying electrosurgical energy thereto.

BRIEF DESCRIPTION OF THE DRAWINGS

Various embodiments of the subject instrument are described herein with reference to the drawings wherein:

FIG. 6 is a partially exploded, perspective view of the end effector assembly;

FIG. 7 is a top view of the end effector assembly with the upper jaw member removed;

DETAILED DESCRIPTION

Figure 1A:
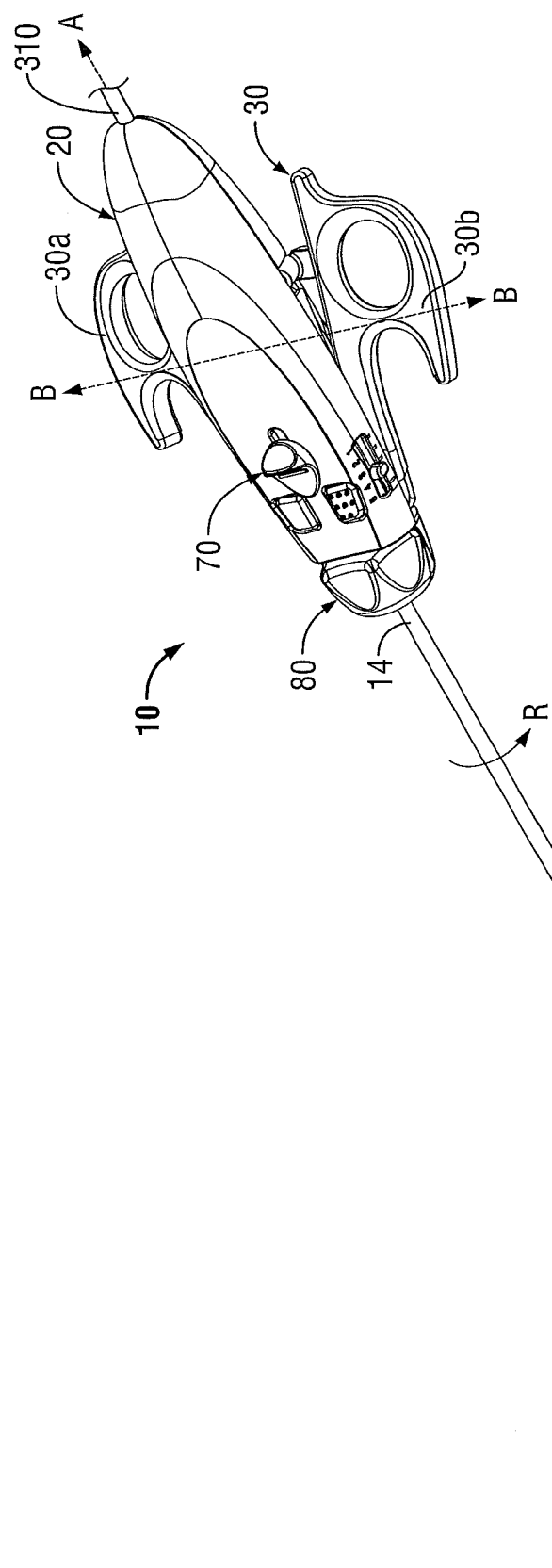
FIG. 1A is a top, perspective view of an endoscopic forceps shown in an open configuration and including a housing, a handle assembly, a shaft and an end effector assembly according to the present disclosure.
Figure 1B:
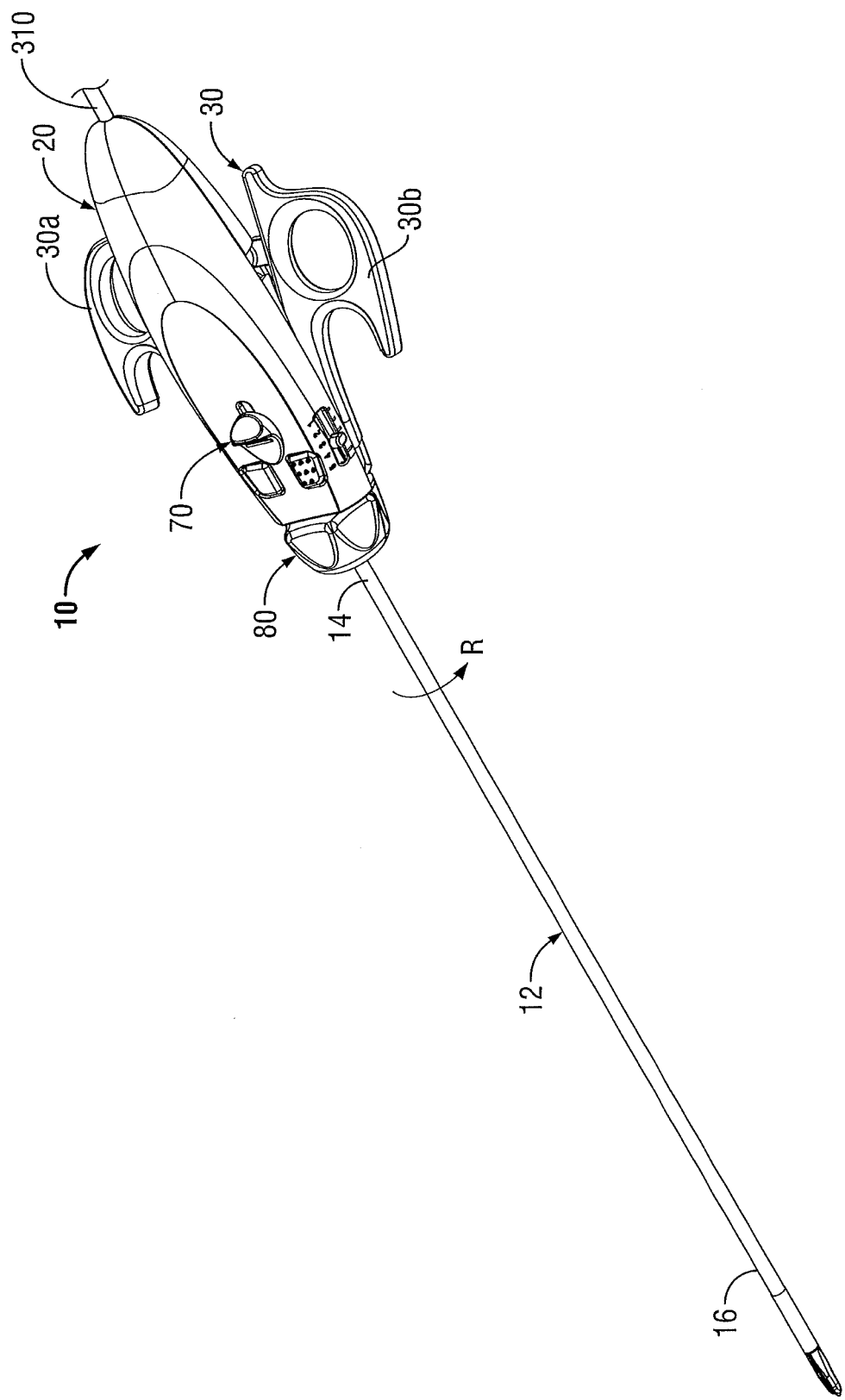
FIG. 1B is a top, perspective view of the endoscopic forceps of FIG. 1A showing the end effector assembly in a closed configuration according to the present disclosure.

Turning now to FIGS. 1A and 1B, one embodiment of an electrosurgical forceps 10 is shown for use with various surgical procedures and generally includes a housing 20, a handle assembly 30, a rotating assembly 80, a knife trigger assembly 70 and an end effector assembly 100 which mutually cooperate to grasp, seal and divide tubular vessels and vascular tissue. Although the majority of the figure drawings depict a forceps 10 for use in connection with endoscopic or laparoscopic surgical procedures, the present disclosure may be used for more traditional open surgical procedures. For the purposes herein, the forceps 10 is described in terms of an endoscopic or laparoscopic instrument; however, it is contemplated that an open version of the forceps may also include the same or similar operating components and features as described below.

Forceps 10 includes a shaft 12 that has a distal end 16 dimensioned to mechanically engage the end effector assembly 100 and a proximal end 14 that mechanically engages the housing 20. Details of how the shaft 12 connects to the end effector assembly 100 are described in more detail below. The proximal end 14 of shaft 12 is received within the housing 20 and the connections relating thereto are also described in detail below. In the drawings and in the descriptions that follow, the term "proximal", as is traditional, will refer to the end of the forceps 10 that is closer to the user, while the term "distal" will refer to the end that is further from the user.

Forceps 10 also includes an electrosurgical cable 310 that may connect the forceps 10 to a source of electrosurgical energy, e.g., a generator. Generators such as those sold by Covidien, located in Boulder, Colo. may be used as a source of both bipolar electrosurgical energy for sealing vessel and vascular tissues as well as monopolar electrosurgical energy which is typically employed to coagulate or cauterize tissue. It is envisioned that the generator may include various safety and performance features including isolated output, impedance control and/or independent activation of accessories.

Handle assembly 30 includes two movable handles 30a and 30b disposed on opposite sides of housing 20. Handles 30a and 30b are movable relative to one another to actuate the end effector assembly 100 as explained in more detail below with respect to the operation of the forceps 10.

Rotating assembly 80 is mechanically coupled to housing 20 and is rotatable approximately 90 degrees in either direction about a longitudinal axis "A." Rotating assembly 80, when rotated, rotates shaft 12, which, in turn, rotates end effector assembly 100. Such a configuration allows end effector assembly 100 to be rotated approximately 90 degrees in either direction with respect to housing 20.

As mentioned above, end effector assembly 100 is attached at the distal end 16 of shaft 12 and includes a pair of opposing jaw members 110 and 120 (see FIG. 6). Handles 30a and 30b of handle assembly 30 ultimately connect to drive assembly 60 (see FIG. 2A) which, together, mechanically cooperate to impart movement of the jaw members 110 and 120 from a first, open position wherein the jaw members 110 and 120 are disposed in spaced relation relative to one another, to a second, clamping or closed position wherein the jaw members 110 and 120 cooperate to grasp tissue therebetween.

Turning now to the more detailed features of the present disclosure as described with respect to FIGS. 1A-8C, handles 30a and 30b each include an aperture 33a and 33b, respectively, defined therein which enables a user to grasp and move each respective handle 30a and 30b relative to one another. Handles 30a and 30b also include ergonomically-enhanced gripping elements 39a and 39b, respectively, disposed along an outer edge thereof which are designed to facilitate gripping of the handles 30a and 30b during activation. It is envisioned that gripping elements 39a and 39b may include one or more protuberances, scallops and/or ribs to enhance gripping.

As best illustrated in FIG. 1A, handles 30a and 30b are configured to extend outwardly on opposite sides from a transverse axis "B" defined through housing 20 which is perpendicular to longitudinal axis "A". Handles 30a and 30b are movable relative to one another in a direction parallel to axis "B" to open and close the jaw members 110 and 120 as needed during surgery. Details relating to the inner-working components of forceps 10 are disclosed in commonly-owned U.S. patent application Ser. No. 11/540,335. This forceps style is commonly referred to as an "in-line" or hemostat style forceps. In-line hemostats or forceps are more commonly manufactured for open surgical procedures and typically include a pair of shafts having integrally coupled handles which are movable relative to one another to open and close the jaw members disposed at the distal end thereof.

Figure 2A:
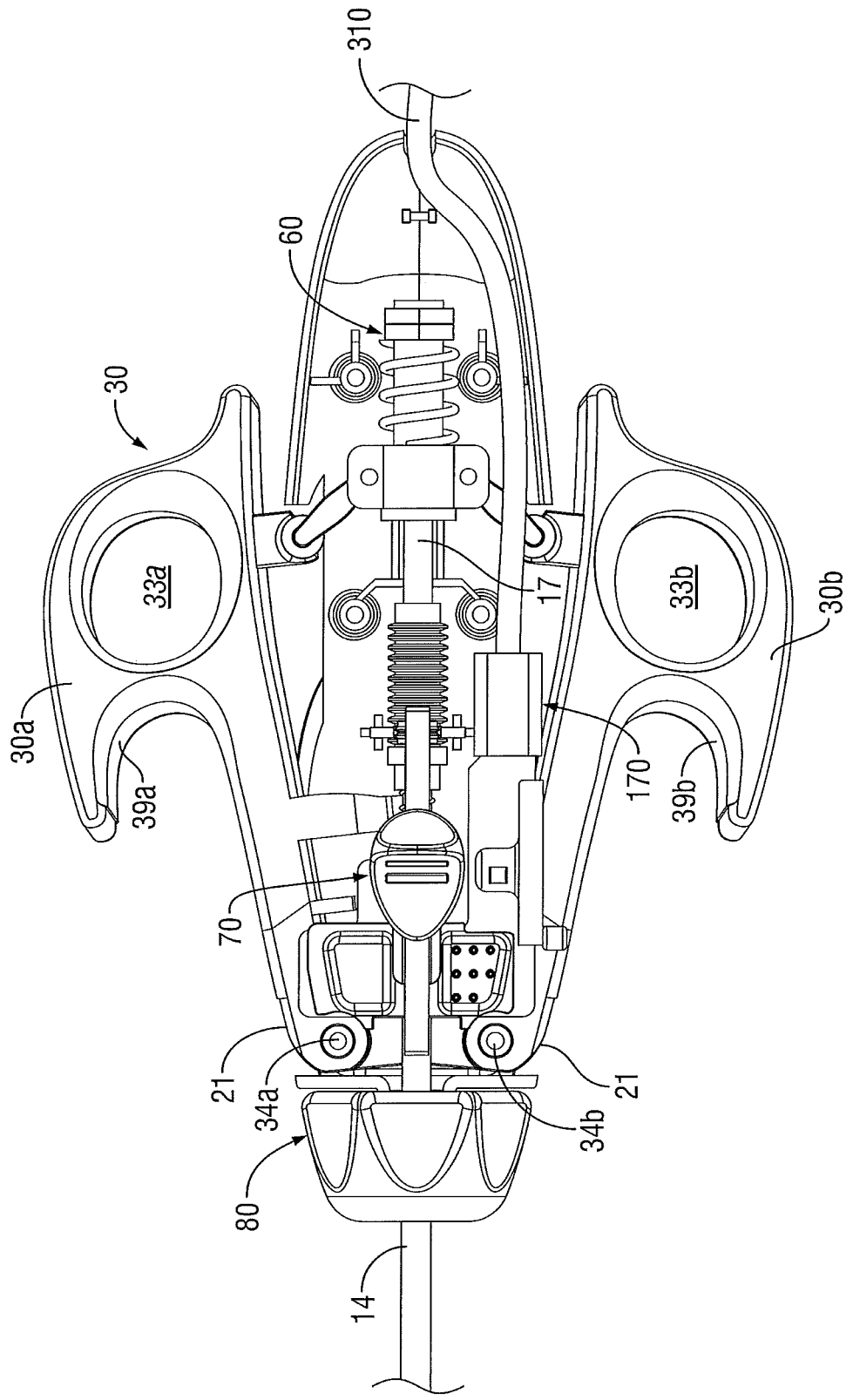
FIG. 2A is an enlarged, top view of the forceps of FIG. 1A showing the disposition of the internal components when the forceps is in an open configuration.
Figure 2B:
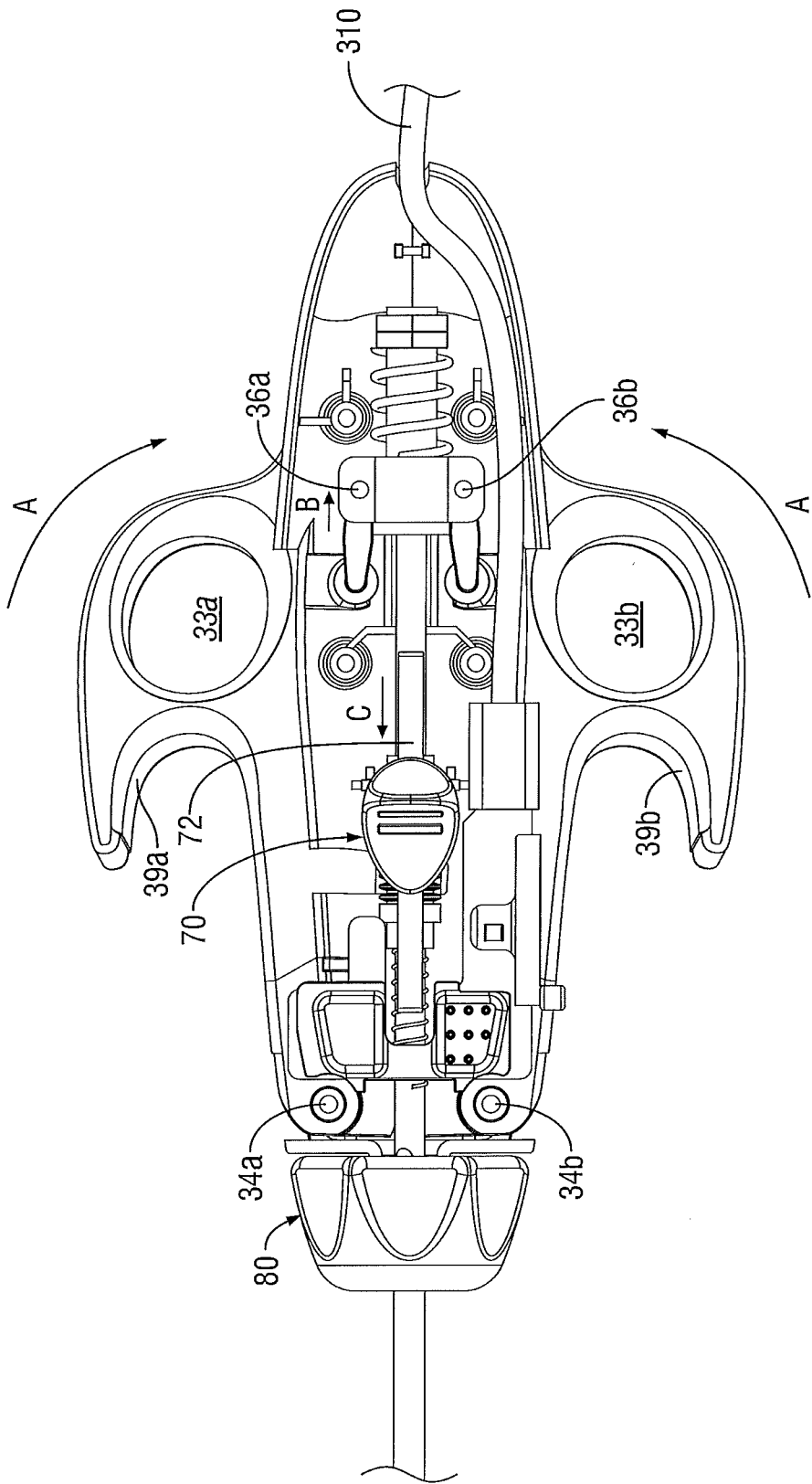
FIG. 2B is an enlarged, top view of the forceps of FIG. 1B showing the disposition of the internal components when the forceps is in a closed configuration.
Figure 3A:
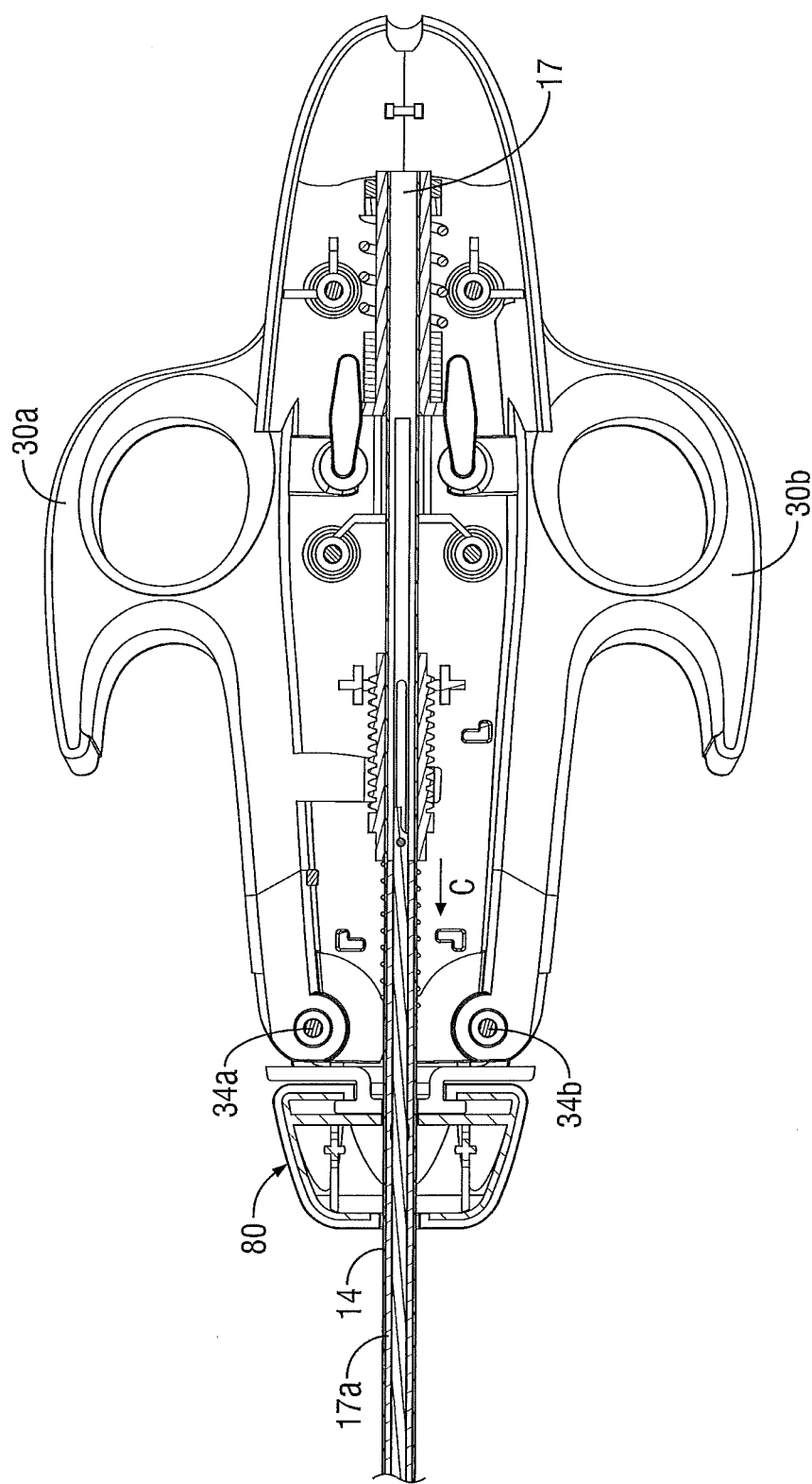
FIG. 3A is an enlarged, top view showing the knife actuator after actuation.
Figure 3B:
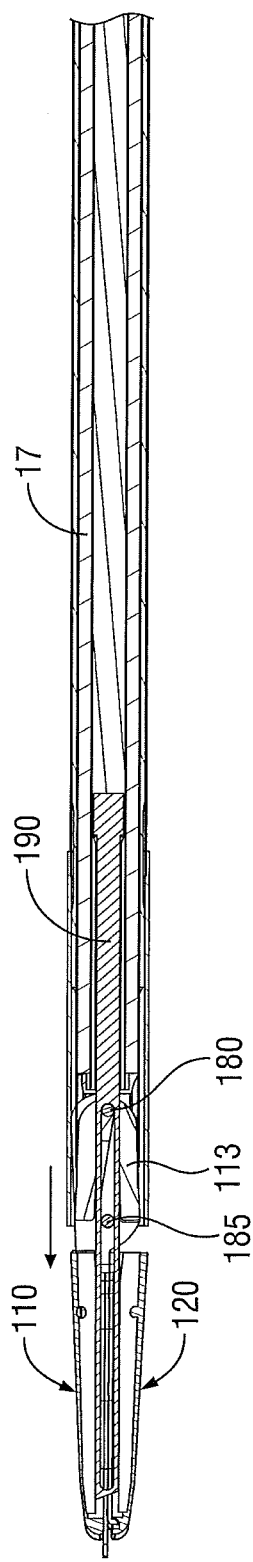
FIG. 3B is a greatly-enlarged, side cross sectional view of the end effector assembly showing the position of the knife after actuation.

As best seen in FIGS. 2A and 2B, the distal end of each handle 30a and 30b is selectively moveable about pivot pins 34a and 34b attached to a distal end 21 of the housing 20 to actuate the jaw members 110 and 120. Movement of the handles 30a and 30b away from one another (and the housing 20) unlocks and opens the handles 30a and 30b and, in turn, the jaw members 110 and 120 for subsequent grasping or re-grasping of tissue. In one embodiment, the handles 30a and 30b may be biased in an open configuration to facilitate handling and manipulation of the jaws within an operative field. Various spring-like mechanisms are contemplated which may be utilized to accomplish this purpose.

Movable handles 30a and 30b are designed to provide a distinct lever-like mechanical advantage over conventional handle assemblies. The enhanced mechanical advantage for actuating the jaw members 110 and 120 is gained by virtue of the unique position and combination of several inter-cooperating elements which reduce the overall user forces necessary to obtain and maintain the jaw members 110 and 120 under ideal operating pressures of about 3 kg/cm$^2$ to about 16 kg/cm$^2$. Details relating to the working components the handle assembly and drive assembly are disclosed in above-mentioned U.S. patent application Ser. No. 11/540,335. In other words, it is envisioned that the combination of these elements and their positions relative to one another enables the user to gain lever-like mechanical advantage to actuate the jaw members 110 and 120 enabling the user to close the jaw members 110 and 120 with lesser force while still generating the required forces necessary to effect a proper and effective tissue seal.

As shown best in FIGS. 4A, 4B, 5 and 6, the end effector assembly 100 is designed as a bilateral assembly, i.e., both jaw members 110 and 120 pivot relative to one another about a pivot pin 185 disposed therethrough. A unilateral end effector assembly is also envisioned. End effector assembly 100 further includes a knife guide 133 that houses the knife blade 190 for translation therethrough. Knife guide 133 is assembled with flanges 113 and 123 to allow pivotable movement of the flanges 113 and 123 about a pivot pin 185 disposed between the jaw members 110 and 120 upon translation of a drive pin 180 as explained in more detail below.

More particularly, jaw members 110 and 120 include proximal flanges 113 and 123, respectively, which each include an elongated angled slot 181a and 181b, respectively, defined therethrough. Drive pin 180 mounts jaw members 110 and 120 and knife guide 133 to the end of a rotating shaft 18 and within a cavity 17' defined at the distal ends 17a and 17b of drive actuator or sleeve 17 (See FIG. 5). Knife guide 133 includes an elongated slot 181c defined therethrough, configured for accepting the drive pin 180 and for allowing translation of the drive pin 180 within slots 181a-181c, which pivots the jaw members 110 and 120 relative to one another for grasping tissue. Knife guide 133 may also provide a unique safety feature for the forceps 10 as described in more detail below.

Upon actuation of the drive assembly 60, the drive sleeve 17 reciprocates which, in turn, causes the drive pin 180 to ride within slots 181a and 181b to open and close the jaw members 110 and 120 as desired and similarly causes the drive pin 180 to ride within slot 181c of knife guide 133. The jaw members 110 and 120, in turn, pivot about pivot pin 185 disposed through respective pivot holes 186a and 186b defined within flanges 113 and 123, the jaw members 110 and 120 and hole 186c disposed within knife guide 133. Upon actuation, knife guide 133 remains oriented in alignment with the shaft 12 as the jaws move about pivot pin 185 (See FIG. 6). As can be appreciated, squeezing handles 30a and 30b toward the housing 20 pulls drive sleeve 17 and drive pin 180 proximally to close the jaw members 110 and 120 about tissue grasped therebetween and pushing the sleeve 17 distally opens the jaw members 110 and 120 for grasping purposes.

Flanges 113 and 123 of jaw members 110 and 120, respectively, are positioned in an abutting relationship with one another and knife guide 133 is positioned adjacent to flanges 113 and 123. Flanges 113, 123 and knife guide 133 are assembled and engaged via pivot pin 185 disposed through apertures 186a, 186b, and 186c, respectively. Further, flanges 113, 123 are pivotable about one another via drive pin 180 disposed through slots 181a and 181b and of flanges 113, 123, respectively. A knife path 138 may be defined between flange 113 and knife guide 133, as shown in FIGS. 6 and 7. The knife path 138 longitudinally aligns with knife channels 115a and 115b defined within jaw members 110 and 120, such that knife blade 190 travels in a substantially straight path through knife path 138 and, further, through knife channels 115a and 115b.

Alternatively, the orientation of flanges 113 and 123 may be reversed, with knife path 138 being defined between flange 123 and blade guide 133. In contrast to prior known designs, the abutting relationship between flanges 113 and 123 (in either orientation) strengthens the jaw flanges 113 and 123 since a blade path or blade channel does not need to be defined therebetween but, rather, is defined on an exterior side of one of the flanges 113 and 123. Thus, the knife 190 travels between the blade guide 133 and the flanges 113 and 123 and not between flanges. By manufacturing the knife path 138 on either side of the flanges 113 and 123, jaw splay may also be more easily controlled and tighter tolerances may be employed during the manufacturing process, thereby allowing tighter tolerances on certain features of the jaw member 110 and 120 resulting in better overall performance.

For example, the knife channels 115a and 115b defined within the jaw members 110 and 120, respectively, may be more precisely aligned with less splay between the jaw members 110 and 120, thereby facilitating knife blade 190 translation. Moreover, the strength of the flanges 113 and 123 is enhanced as well as the union therebetween, e.g., flat-on-flat abutting flange surfaces have more surface contact making the union therebetween stronger. The knife guide 133 may also be configured to pre-load jaw members 110 and 120 to help ensure proper alignment of knife channel halves 115a and 115b upon closing of the jaw members 110 and 120 as explained in more detail below.

As best shown in FIG. 6, blade guide 133 may include a blade stop or hook 135 disposed at a distal end thereof. The blade stop 135 may be integrally associated with the knife guide 133 (FIG. 6), the purpose of which is explained immediately below, or pivotably engaged with the knife guide 133, the purpose of which is explained with reference to FIG. 9. The relationship between flanges 113 and 123 and blade guide 133 is established by pivot pin 185 disposed through apertures 186a, 186b, and 186c, respectively, and by drive pin 180 disposed through slots 181a, 181b and 181c, respectively. Accordingly, when jaw members 110, 120 are in a first, or open, position, knife guide 133 pivots such the blade stop 135 interferes with the knife path 138, thereby preventing distal translation of knife blade 190. In one embodiment, this may be accomplished by the knife guide 133 including an elongated slot 181c that is cammed when the drive pin 180 is biased in a distal-most position such that the knife guide 133 and blade stop 135 pivot thereby obstructing the knife path 138. Alternatively, the blade stop 135 may pivot relative to the knife guide 133 to obstruct the knife path 138 (See FIG. 9). In this instance, the elongated slot 181c may be constructed as a pass-through or non-engaging slot.

When handles 30a and 30b are squeezed toward the housing 20, drive sleeve 17 and drive pin 180 are pulled proximally to close the jaw members 110 and 120, which also pivots the knife guide 133 so that the blade stop 135 no longer obstructs or interferes with the knife path 138. Thus, in this embodiment, the knife guide 133, by virtue of the blade stop 135, prevents distal advancement of knife blade 190 when jaw members 110 and 120 are in the first, open position and permits distal advancement of knife blade 190 when jaw members 110 and 120 are in the second, closed position.

Alternatively, a hook (not shown) may be disposed on either of flanges 113 or 123. The hook would operate in substantially the same manner as the blade stop 135 disposed on the blade guide 133 in the embodiment discussed above. Accordingly, as jaw members 110, 120 are opened, the hook on flange 113 or 123 is pivoted into the path of knife blade 190, thereby preventing distal translation of knife blade 190. When handles 30a and 30b are squeezed toward the housing 20, drive sleeve 17 and drive pin 180 are pulled proximally to close the jaw members 110 and 120. The pulling of drive pin 180 also pivots flanges 113 and 123, thereby closing the jaw members 110 and 120 and as a result, the hook is pivoted out of the path of knife blade 190.

Figure 4A:
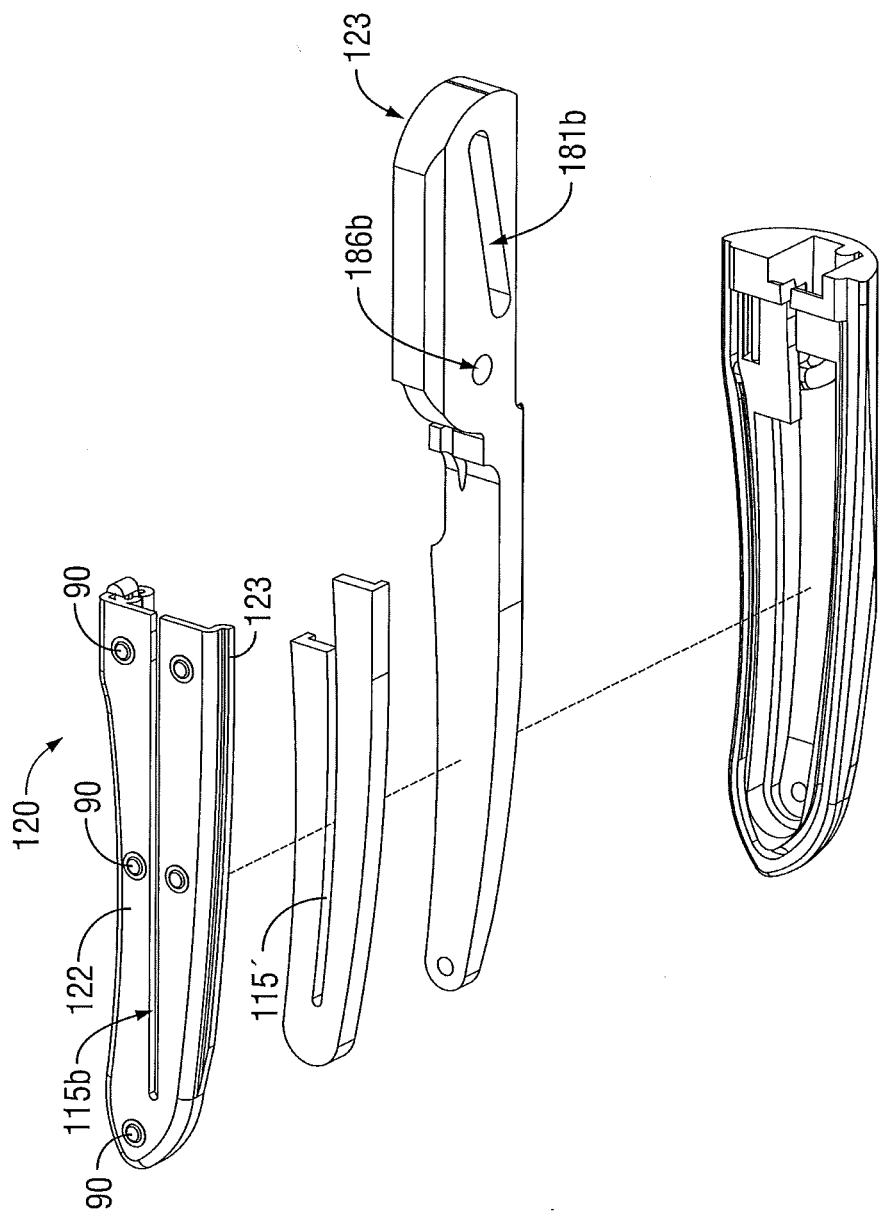
FIG. 4A is a greatly-enlarged, perspective view of the bottom jaw of the end effector assembly with parts separated.
Figure 4B:
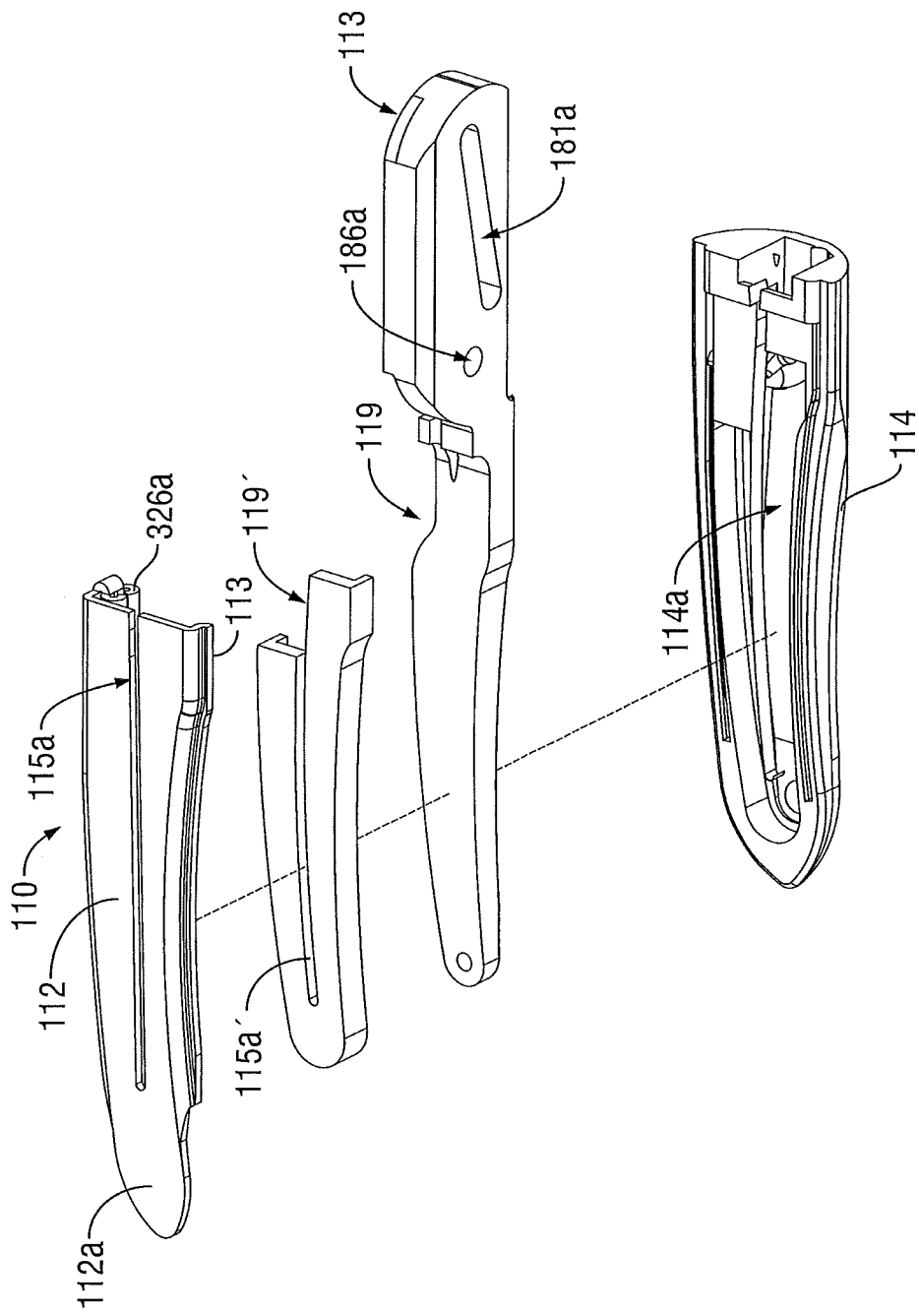
FIG. 4B is a greatly-enlarged, perspective view of the top jaw of the end effector assembly with parts separated.
Figure 5:
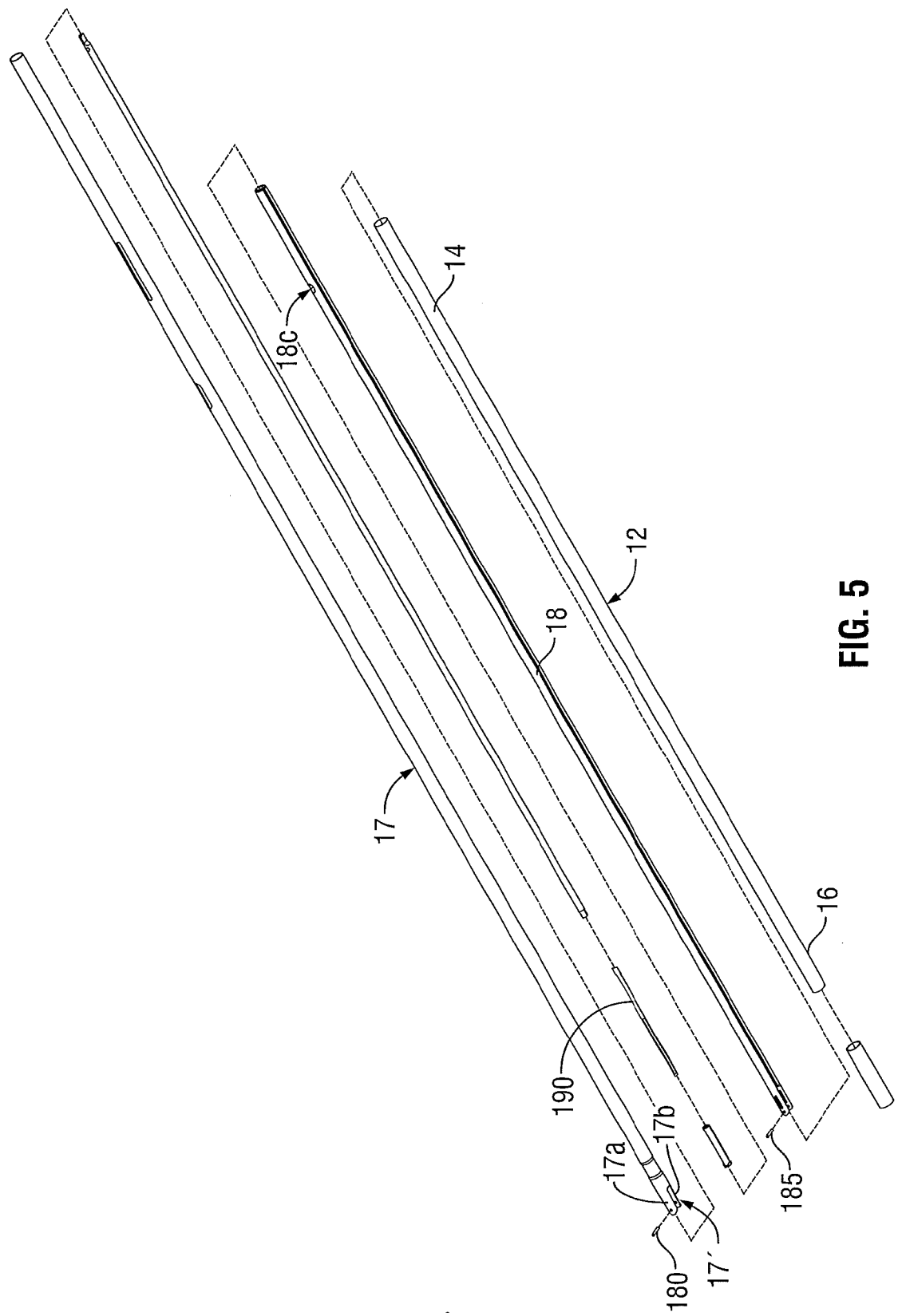
FIG. 5 is a greatly-enlarged, perspective view of the elongated shaft for housing various moving parts of the drive assembly and knife assembly.

As best shown in FIG. 4B, jaw member 110 also includes a support base 119 that extends distally from flange 113 and that is configured to support an insulative plate 119' thereon. Insulative plate 119', in turn, is configured to support an electrically conductive tissue engaging surface or sealing plate 112 thereon. Sealing plate 112 may be affixed atop the insulative plate 119' and support base 119 in any suitable manner, e.g., snap-fit, over-molding, stamping, ultrasonically welded, etc. Support base 119 together with the insulative plate 119' and electrically conductive tissue engaging surface 112 are encapsulated by an outer insulative housing 114. Outer housing 114 includes a cavity 114a that is dimensioned to securely engage the electrically conductive sealing surface 112 as well as the support base 119 and insulative plate 119'. This may be accomplished by stamping, by overmolding, by overmolding a stamped electrically conductive sealing plate and/or by overmolding a metal injection molded seal plate. All of these manufacturing techniques produce jaw member 110 having an electrically conductive surface 112 that is substantially surrounded by an insulating substrate 114.

The electrically conductive surface or sealing plate 112 and the outer housing 114, when assembled, form longitudinally-oriented knife channel 115a defined therethrough for reciprocation of the knife blade 190. It is envisioned that the knife channel 115a cooperates with corresponding knife channel 115b defined in jaw member 120 to facilitate longitudinal extension of the knife blade 190 along a preferred cutting plane to effectively and accurately separate the tissue along the formed tissue seal. As discussed above, when knife blade 190 is deployed, at least a portion of knife blade 190 advances through knife path 138 and into knife channels 115a and 115b. In addition to the blade stop 135, handle 30a may includes a lockout flange (not shown) which prevents actuation of the knife assembly 70 when the handle 30a is open thus preventing accidental or premature activation of the knife blade 190 through the tissue. A more detailed discussion of the lockout flange is discussed in above-mentioned U.S. patent application Ser. No. 11/540,335.

As explained above and as illustrated in FIGS. 4A and 4B, in one embodiment, the knife channel 115 is formed when the jaw members 110 and 120 are closed. In other words, the knife channel 115 includes two knife channel halves—knife channel half 115a disposed in sealing plate 112 of jaw member 110 and knife channel half 115b disposed sealing plate 122 of jaw member 120. It is envisioned that the knife channel 115 may be configured as a straight slot with no degree of curvature which, in turn, causes the blade 190 to move through the tissue in a substantially straight fashion. Alternatively, and as shown, the knife channel 115 may be curved, which has certain surgical advantages. In the particular embodiment shown in FIGS. 6 and 7, the knife channel 115 (knife channel 115a shown) is curved and is offset from the centerline or longitudinal axis "A" of the forceps 10 by a distance "X" (See FIGS. 7 and 8). This offset distance "X" may be in the range of about 0.010 inches to about 0.040 inches.

The offset orientation of the knife blade 190 (by virtue or the knife guide 133 being assembled on one side of the flanges 113 and 123 allows the knife blade to enter the knife channel 115 in a substantially straight orientation thereby facilitating separation of tissue. Moreover, the knife blade 190 travels in a substantially straight manner through most of the knife channel 115 and is only forced to bend around the knife channel 115 towards a distal end of the jaw members 110 and 120. Further, the offset orientation of the knife channel, e.g., knife channel 115b, and the disposition of the knife blade 190 traveling through the knife guide 133 also enhances the cutting effect and reduces the chances of the knife blade 190 binding during translation (extension or retraction).

As mentioned above, when the jaw members 110 and 120 are closed about tissue, knife channels 115a and 115b form a complete knife channel 115 to allow longitudinal extension of the knife blade 190, from the knife path 138, in a distal fashion to sever tissue along a tissue seal. Knife channel 115 may be completely disposed in one of the two jaw members, e.g., jaw member 120, depending upon a particular purpose.

It is also envisioned that jaw member 120 may be assembled in a similar manner as described above with respect to jaw member 110.

Figure 8:
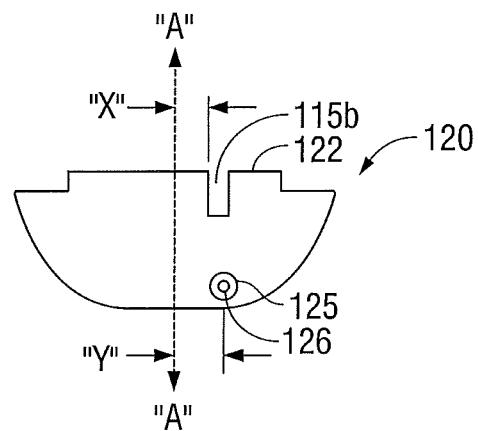
FIG. 8 is a rear, perspective view of one of the jaw members in accordance with an alternate embodiment of the present disclosure.

Referring now to FIGS. 6 and 8, electrical lead or wire 126 is shown extending from shaft 12 through knife housing 133 and entering wire tube 125 of jaw members 120. Wires 116 and 126 are used to supply electrical energy to electrically conductive sealing surfaces 112 and 122 of jaw members 110 and 120, respectively. In the embodiment of FIG. 6, knife housing 133 also acts as a wire guide, configured to guide wires 116 and 126 to jaw members 110 and 120. Electrical leads or wires 116 and 126 are protected by knife housing 133. Wire tube 125 (FIG. 8) of jaw member 120, may be offset from a longitudinal axis "Y" of the forceps 10 in the same direction as the offset knife channel 115*b*, such that knife channel 115*b* is disposed above the wire tube 125. The offset "X" of the knife channel, e.g., knife channel 115*b*, and the offset "Y" of the disposition of the electrical lead or wire 126 relative to longitudinal axis "A" may be different or the same depending upon a particular purpose or to facilitate manufacturing. For example, as mentioned above, the offset distance "X" may be in the range of about 0.010 inches to about 0.040 inches whereas the offset distance "Y" may be in the range about 0.040 inches to about 0.140 inches. In addition, particular "X" and "Y" configurations may be as follows: When "X" is about 0.010 inches "Y" may be about 0.040 inches; when "X" is about 0.017 inches "Y" may be about 0.070 inches; and when "X" is about 0.034 inches "Y" may be about 0.140 inches. Other configurations and offsets for "X" and "Y" are also contemplated and within the scope of this disclosure.

Figure 9:
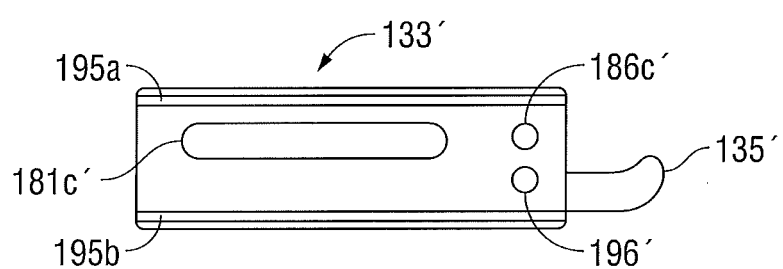
FIG. 9 is an enlarged side view of another embodiment of the knife guide according to the present disclosure.

FIG. 9 shows another embodiment of the knife guide 133' that includes similar features to the knife guide 133 described above such as elongated slot 181*c'*, pivot hole 186*c'* and blade stop 135'. In this particular embodiment, the blade stop is moveable from a first position that interferes with the knife path 138 (See FIG. 7) to prevent distal translation of the knife 190 when the jaw members 110 and 120 are disposed in an first, open configuration to a second position that allows distal translation of the knife 190 when the jaw members 110 and 120 are disposed in the second, closed configuration. The blade stop 135' is pivotably engaged to the knife guide 133' and biased to obstruct with the knife path 138 when the jaw members 110 and 120 are disposed in the first, open configuration. Thus in this embodiment, the blade stop 135 prevents distal advancement of knife blade 190 when jaw members 110 and 120 are in the first, open configuration and permits distal advancement of knife blade 190 when jaw members 110 and 120 are in the second, closed configuration.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An end effector assembly for a surgical instrument, comprising:

first and second jaw members each including a proximal flange defining an inwardly-facing surface, a jaw body extending distally from the proximal flange, and an electrically-conductive tissue-engaging surface disposed on each jaw body in opposed relation relative to one another, the proximal flanges coupled to one another and configured to move the jaw bodies relative to one another between a first position, in spaced relation relative to one another, and a second position, for grasping tissue between the tissue-engaging surfaces, the inwardly-facing surfaces of the proximal flanges disposed in abutting relation relative to one another;

a first electrical lead adapted to connect to a source of electrosurgical energy, the first electrical lead extending adjacent an outer surface of one of the proximal flanges and electrically coupled to one of the electrically-conductive tissue-engaging surfaces for communicating energy to tissue grasped between the tissue-engaging surfaces; and a pivot pin pivotably coupling the proximal flanges to one another such that the jaw bodies are pivotable relative to one another between the first position and the second position, wherein each proximal flange defines a cam slot extending therethrough, and wherein a drive pin is operably engaged within the cam slots, the drive pin selectively translatable along the cam slots to pivot the jaw bodies between the first position and the second position.

2. The end effector assembly according to claim 1, wherein each jaw body defines a longitudinal axis and wherein the proximal flange of each jaw body is offset relative to the longitudinal axis of the respective jaw body.

3. The end effector assembly according to claim 2, wherein the first electrical lead is coupled to the electrically-conductive tissue-engaging surface on an opposite side of the longitudinal axis as compared to the proximal flange.

4. The end effector assembly according to claim 1, further comprising a second electrical lead, the first electrical lead extending adjacent the outer surface of one of the proximal flanges to electrically couple to the electrically-conductive tissue-engaging surface of the first jaw member and the second electrical lead extending adjacent the outer surface of the same proximal flange to electrically couple to the electrically-conductive tissue-engaging surface of the second jaw member.

5. The end effector assembly according to claim 1, wherein each of the jaw bodies includes a support base extending distally from the respective proximal flange, an insulator supported on the support base, and an electrically-conductive tissue-engaging plate supported on the insulator, the electrically-conductive tissue-engaging plate defining the electrically-conductive tissue-engaging surface of the jaw body.

6. The end effector assembly according to claim 5, wherein each of the jaw bodies further includes an insulative jaw housing disposed about the support base and insulator thereof.

7. The end effector assembly according to claim 1, wherein one of the jaw bodies defines a lumen extending therethrough, the first electrical lead extending through the lumen to electrically couple to the electrically-conductive tissue-engaging surface.

8. The end effector assembly according to claim 7, wherein the lumen is offset relative to a longitudinal axis defined through the jaw body.

9. An end effector assembly for a surgical instrument, comprising:

first and second jaw members defining opposed electrically-conductive tissue-engaging surfaces, each jaw member including a proximal flange defining an inwardly-facing surface, a jaw body extending distally from the proximal flange, and an electrically-conductive tissue-engaging surface disposed each jaw body in opposed relation relative to one another, the proximal flanges coupled to one another and configured to move the jaw bodies relative to one another between a first position, in spaced relation to one another, and a second position, for grasping tissue between the tissue-engaging surfaces, the inwardly-facing surfaces of the proximal flanges disposed in abutting relation relative to one another;

a guide positioned adjacent an outer surface of one of the proximal flanges;

at least one electrical lead adapted to connect to a source of electrosurgical energy, the at least one electrical lead extending through the guide and electrically coupled to at least one of the electrically-conductive tissue-engaging surfaces for communicating energy to tissue grasped between the tissue-engaging surfaces; and a pivot pin pivotably coupling the proximal flanges to one another such that the jaw bodies are pivotable relative to one another between the first position and the second position, wherein each proximal flange defines a cam slot extending therethrough, and wherein a drive pin is operably engaged within the cam slots, the drive pin selectively translatable along the cam slots to pivot the jaw bodies between the first position and the second position.

10. The end effector assembly according to claim 9, wherein each jaw body defines a longitudinal axis and wherein the proximal flange of each jaw body is offset relative to the longitudinal axis of the respective jaw body.

11. The end effector assembly according to claim 10, wherein each of the at least one electrical leads is coupled to the electrically-conductive tissue-engaging surface on an opposite side of the longitudinal axis as compared to the proximal flange of the respective jaw body.

12. The end effector assembly according to claim 9, wherein first and second electrical leads are provided, the first electrical lead extending through the guide and electrically coupled to the electrically-conductive tissue-engaging surface of the first jaw member, the second electrical lead extending through the guide and electrically coupled to the electrically-conductive tissue-engaging surface of the second jaw member.

13. The end effector assembly according to claim 9, wherein each of the jaw bodies includes a support base extending distally from the respective proximal flange, an insulator supported on the support base, and an electrically-conductive tissue-engaging plate supported on the insulator, the electrically-conductive tissue-engaging plate defining the electrically-conductive tissue-engaging surface of the jaw body.

14. The end effector assembly according to claim 13, wherein each of the jaw bodies further includes an insulative jaw housing disposed about the support base and insulator thereof.

15. The end effector assembly according to claim 9, wherein one of the jaw bodies defines a lumen extending therethrough, the at least one electrical lead extending from the guide through the lumen to electrically couple to the electrically-conductive tissue-engaging surface.

16. The end effector assembly according to claim 15, wherein the lumen is offset relative to a longitudinal axis defined through the jaw body.

17. An end effector assembly for a surgical instrument, comprising:

first and second jaw members each including a proximal flange defining an inwardly-facing surface, a jaw body extending distally from the proximal flange, and an electrically-conductive tissue-engaging surface disposed on each jaw body in opposed relation relative to one another, the proximal flanges coupled to one another and configured to move the jaw bodies relative to one another between a first position, in spaced relation relative to one another, and a second position, for grasping tissue between the tissue-engaging surfaces, the inwardly-facing surfaces of the proximal flanges disposed in abutting relation relative to one another; and a first electrical lead adapted to connect to a source of electrosurgical energy, the first electrical lead extending adjacent an outer surface of one of the proximal flanges and electrically coupled to one of the electrically-conductive tissue-engaging surfaces for communicating energy to tissue grasped between the tissue-engaging surfaces, wherein one of the jaw bodies defines a lumen extending therethrough, the first electrical lead extending through the lumen to electrically couple to the electrically-conductive tissue-engaging surface.

18. The end effector assembly according to claim 17, wherein the lumen is offset relative to a longitudinal axis defined through the jaw body.

19. An end effector assembly for a surgical instrument, comprising:

first and second jaw members defining opposed electrically-conductive tissue-engaging surfaces, each jaw member including a proximal flange defining an inwardly-facing surface, a jaw body extending distally from the proximal flange, and an electrically-conductive tissue-engaging surface disposed each jaw body in opposed relation relative to one another, the proximal flanges coupled to one another and configured to move the jaw bodies relative to one another between a first position, in spaced relation to one another, and a second position, for grasping tissue between the tissue-engaging surfaces, the inwardly-facing surfaces of the proximal flanges disposed in abutting relation relative to one another;

a guide positioned adjacent an outer surface of one of the proximal flanges; and at least one electrical lead adapted to connect to a source of electrosurgical energy, the at least one electrical lead extending through the guide and electrically coupled to at least one of the electrically-conductive tissue-engaging surfaces for communicating energy to tissue grasped between the tissue-engaging surfaces, wherein one of the jaw bodies defines a lumen extending therethrough, the at least one electrical lead extending from the guide through the lumen to electrically couple to the electrically-conductive tissue-engaging surface.

20. The end effector assembly according to claim 19, wherein the lumen is offset relative to a longitudinal axis defined through the jaw body.

* * * * *